(12) United States Patent
Hirokawa

(10) Patent No.: US 6,464,679 B1
(45) Date of Patent: Oct. 15, 2002

(54) DISPOSABLE DIAPER

(75) Inventor: Norinaka Hirokawa, Toyama-ken (JP)

(73) Assignee: YKK Corporation, Tokyo (JP)

( * ) Notice: Subject to any disclaimer, the term of this patent is extended or adjusted under 35 U.S.C. 154(b) by 104 days.

(21) Appl. No.: 09/628,529

(22) Filed: Jul. 31, 2000

(30) Foreign Application Priority Data

Aug. 10, 1999 (JP) .......................................... 11-226035

(51) Int. Cl.⁷ ................................................ A61F 13/15
(52) U.S. Cl. ...................... 604/390; 604/391; 604/386; 604/387; 604/389; 604/390
(58) Field of Search ............................ 604/390, 385.01, 604/391, 389, 387, 386, 358

(56) References Cited

U.S. PATENT DOCUMENTS 5,366,453 A * 11/1994 Zehner et al. .............. 604/358
5,496,298 A * 3/1996 Kuepper et al. ............ 604/358
5,695,488 A * 12/1997 Sosalla .................. 604/385.24
5,899,896 A * 5/1999 Suprise et al. .............. 604/358

* cited by examiner

*Primary Examiner*—Rodney M. Lindsey
*Assistant Examiner*—Angela J Grayson
(74) *Attorney, Agent, or Firm*—Finnegan, Henderson, Farabow, Garrett, & Dunner, LLP

(57) ABSTRACT

A disposable diaper has a diaper body having a hip portion and a belly portion, which are spread out with a crotch portion between them. The disposable diaper includes slits defined in side portions of one of the hip portion and the belly portion and connecting members provided on side portions of the other one of the belly portion and the hip portion to be elongated outwardly. The disposable diaper further includes holding means for connecting the hip portion and the belly portion by means of the connecting members. Therefore, the disposable diaper is easy for the wearer to put on, and can be put on easily while the wearer stands on both legs.

3 Claims, 2 Drawing Sheets

DISPOSABLE DIAPER

BACKGROUND OF THE INVENTION

1. Field of the Invention

The present invention relates to a disposable diaper, which is to be disposed after used.

2. Description of the Related Art

As a conventional disposable diaper, there is a spread out type disposable diaper that is designed with a hip portion to cover a wearer's hip and a belly portion to cover the wearer's belly. In this spread out type disposable diaper, the hip portion and the belly portion are separated in a spread out form and are freely attachable/detachable at a waist portion. The spread out type disposable diaper comprises a sheet-shaped diaper body that encloses an absorbent polymer or the like therein. When the wearer uses this diaper, the sheet-shaped diaper body is formed three-dimensionally so as to be a pants-like shape. The spread out type disposable diaper is provided with the-diaper body, the hip portion and the belly portion as an integral portion. At both sides of the hip portion, an adhesive tape is attached so as to extend sideways. The adhesive tapes are stored in tentative attaching portions made of film or the like, which are provided on the hip portion before assembling the diaper. When the diaper is put on, the adhesive tapes are adhered to the belly portion.

There is also a conventional pants-shaped diaper. that has been used. This pants-shaped disposable diaper is designed such that the wearer can put it on, as the wearer is standing. The wearer has his legs inserted into leg through holes respectively from the inside to the outside likewise and can pull it up to his waist, likewise he puts pants on.

Further, a disposable diaper with a waist holding member in a belt shape is disclosed in Japanese Patent, Laid-Open Publication No. 10-57415. This disposable diaper is provided with a pair of waist holding members at right and left sides of a back of a diaper body. A fastening portion is provided to an end of each waist holding member. Further, one of the waist holding members has a slit defined between the fastening portion for the waist holding member and a base end portion of the waist holding member. A diaper fastening portion is provided each of right and left portions of a belly-portion side of the body. Surface fasteners or the like are provided on the fastening portions for the waist holding members and the diaper fastening portions.

A method for using the above disposable diaper is as follows; at first, one of the waist holding members is inserted through the slide of the other one of the waist holding members from the inside to the outside so that the both waist holding members are overlapped to make an annular shape. Then, the respective fastening portions for the waist holding members are engaged with the base end portions of the other corresponding waist holding members to wrap a waist of the wearer. The belly side of the diaper is folded back along the wearer's crotch to cover the wearer's belly. Then, the diaper fastening portions are engaged with the waist holding members. Thus, the wearer can put it on.

The above-described conventional art involves a problem such that the wearer cannot put on the disposable diaper of the spread out type in his standing posture so that the wearer has to lie on the back in order to put it on. Therefore, it is very bother for the wearer to put it on. Further, a space where the wearer can lies down, is required for putting on the diaper, so that it is very difficult to put on the diaper when the wearer stays out. As for a pants shape diaper, on the other hand, although it is possible for the wearer to attach or detach it in a standing posture, it is difficult for the wearer to attach or detach it with putting his shoes on because he has to have his legs inserted into the leg through holes from the inside to the outside. On the other hand, the disposable diaper of the spread out type disclosed in Japanese Patent Laid-Open Publication No. 10-57415 involves a problem such that it is bother for the wearer to put it on since there are many components such as the waist holding members or the like.

SUMMARY OF THE INVENTION

The present invention has been made in view of the foregoing problem. An object of the invention is to provide a disposable diaper, which is easy for the wearer to put on, and which is possible to be put on easily while the wearer is standing on both legs.

The present invention provides a disposable diaper comprising a diaper body including a hip portion and a belly portion, which are spread out with a crotch portion between them, a slit defined in a side portion of one of the hip portion and the belly portion, a connecting member provided on a side portion of the other one of the belly portion and the hip portion to be elongated outwardly, and a holding means for connecting the hip portion and the belly portion by means of the connecting members when the connecting member are inserted into the slit and folded back.

The above holding means comprises surface fasteners disposed on a face to be an inner surface when the connecting member is folded back and on a base end portion of the connecting member, and the surface fasteners are adapted to be engaged with each other. Alternatively, adhesives or the like may be adhered in place of the surface fasteners, which are provided on the side to be inner surfaces when the above connecting members are folded back. The above holding means may be also provided on circumference of the above slit.

In order to put on the disposable diaper according to the present invention, the above connecting members are positioned at the outside of the wearer's legs and are inserted in the slit. The connecting members are folded back respectively to be held on the diaper body by means of the holding means, so that the hip portion and the belly portion of the diaper body are connected at the both sides thereof. Thus, the disposable diaper of the present invention is provided with a pair of leg through holes as the wearer has his legs inserted into the holes. Therefore, the disposable diaper of the present invention can be formed three-dimensional shape for use. In a state where the wearer has his legs inserted into the holes, it is possible to pull up the disposable diaper to the wearer's waist.

DESCRIPTION OF THE EMBODIMENTS

Figure 1:
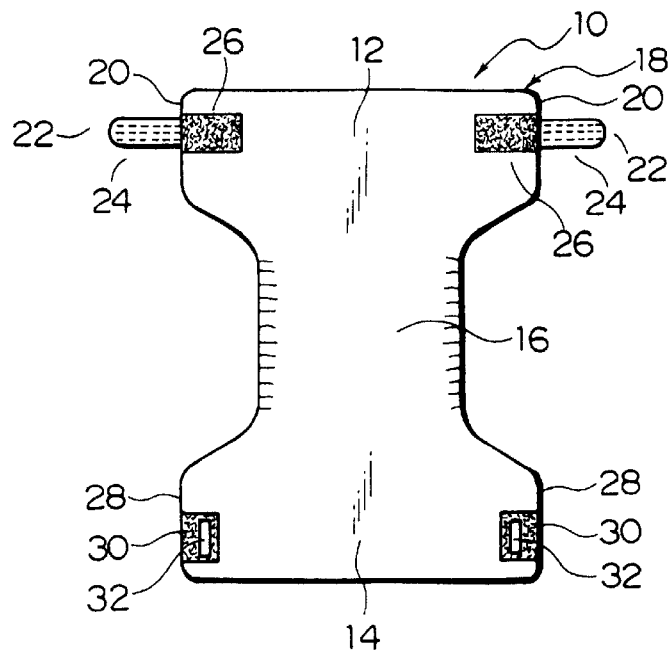
FIG. 1 is a front view of a disposable diaper according to a first embodiment of the present invention.
Figure 2:
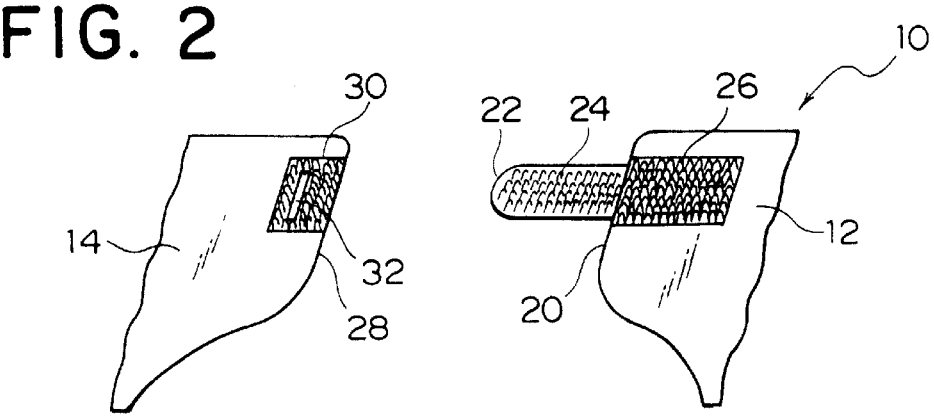
FIG. 2 is a partial perspective view for showing a step of assembling the disposable diaper according to the present embodiment.
Figure 3:
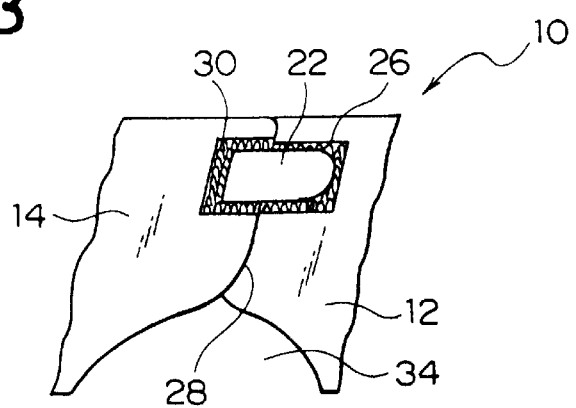
FIG. 3 is a partial perspective view for showing a state in which the disposable diaper according to the present embodiment is assembled.

Embodiments of the present invention will be explained in detail below with reference to the drawings. FIGS. 1 to 3 shows the first embodiment of the present invention. A disposable diaper 10 according a first embodiment of the present invention comprises a diaper body 18, which is integrally composed of a hip portion 12 to cover a wearer's hip, a belly portion 14 to cover the wearer's belly and a narrow crotch portion 16 to be positioned between the hip portion 12 and the belly portion 14. The diaper body 18 is structured such that a waterproof cover sheet is provided on an outer surface thereof and an absorbent body made of an absorbent polymer is disposed, namely, a side which a body of the wearer touches. Further, a liquid-permeable sheet is disposed on a surface of the absorbent body. FIG. 1 shows the diaper body 10 only with a view of the outer surface, namely only with a view of the cover sheet.

Both side portions 20 of the hip portion 12 are provided with connecting members 22, respectively which are elongated to opposite sides and which are in flat strip shapes. Hook portions 24 of surface fasteners are respectively disposed on the outer sides, namely, cover-sheet sides, of the connecting members 22. The hook portions 24 serve as holding means for engaging with the connecting members 22 after folded back. Further, loop portions 26 of the surface fasteners are provided in the vicinity of the base end portions of the connecting members 22 on outer sides, namely the cover-sheet sides, of the hip portion 22. The loop portions 26 are slightly larger than the connecting members 22. The connecting members 22 are folded back at the side portions 20 of the hip portion 12 before use. The hook portions 24 and the loop portions 26 are engaged with each other to be overlapped and stored on outer surfaces of the hip portion 12.

At both side portions 28 of the belly portion 14, loop portions 30 of surface fasteners are disposed on outer surfaces of the belly portion 14 so as to be opposed to the vicinity of the base end portions of the connecting members 22. The loop portions 30 has slits 32, which are disposed in parallel with the side portions 28. The slits 32 penetrate through the diaper body 18. The slits 32 are biased toward a center of the belly portion 14 from edges of the side portions 28 of the belly portion 14.

A method for using the disposable diaper 10 according to the present embodiment will be explained below. At first, in a state where an infant as a wearer is standing, the crotch portion 16 of the diaper body 18 is positioned between his both legs near the ankles of the legs of the wearer. Further, the connecting members 22 of the hip portion 12 are inserted in the slits 32 of the belly portion 14 via outsides of the wearer's legs. The connecting members 22 are inserted through the inside of the bell portion 14 to the outside thereof. Front ends of the connecting members 22, which stick out from the slits 32, are folded back at the edge of the slits 32 toward the hip portion 12. The hook portions 24 of the connecting members 22 come in contact with the loop portions 26 and 30 under pressure so that the hook portions 24 and the loop portions 26 are engaged with each other. As a result, in the diaper body 18, the side portions 20 of the hip portion 12 and the side portions 28 of the belly portion 14 are connected to each other at the outsides of the wearer's legs. Accordingly, the diaper body 18 obtains a three dimensional shape for use. At this time, the wearer's legs are inserted into leg through holes 34, which are defined by bending the diaper body 18. In this state, the wearer can pull the disposable diaper 10 up to a waist of the wearer to be fixed thereto.

According to the disposable diaper 10 of the present embodiment, it is possible to easily form a spread out type diaper into a three dimensional shape in a state that the wearer is standing. Since the connecting members 22 can be connected so tightly that it can not be easily detached, the wearer can pull up the diaper to his waist, just like he can do to a pants type. Further, when the disposable diaper 10 is assembled, the leg through holes 34 can be defined while the wearer is standing and makes his legs insert into the leg through holes 34. Therefore, while the wearer has his shoes on, he can put on the disposable diaper 10 easily. Further, even when the wearer puts on the disposable diaper 10, sand or the like does not enter the diaper. Furthermore, when the disposable diaper 10 is put on, the connecting members 22 are inserted into the slits 32, so that positioning of height of the hip portion 12 and the belly portion 14 can be reliably performed each other. As a result, it is easy to form the disposable diaper 10 into an appropriate shape. Since the slits 32 are formed on the side portions 28 and the loop portions 30 of the surface fasteners and reinforced, they are so tough that they can connect the side portions 20 and 28 tightly and reliably.

Figure 4:
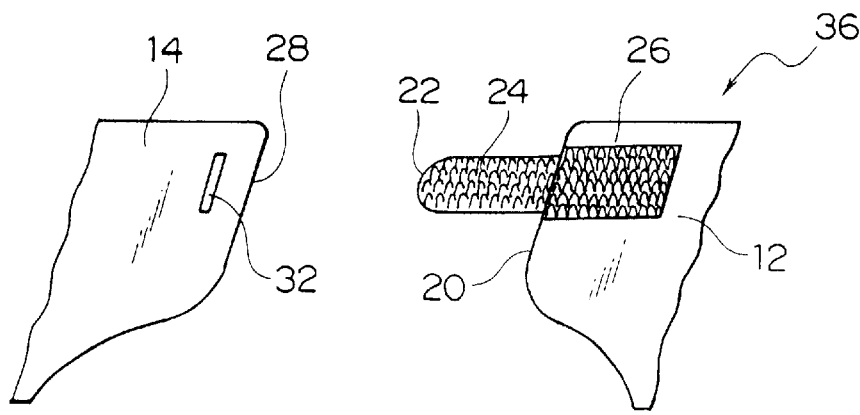
FIG. 4 is a partial perspective view of a disposable diaper according to a second embodiment of the present invention.

A second embodiment of the present invention will be explained with reference to FIG. 4. With respect to the same members as those in the first embodiment, explanation is omitted and the same reference numbers as those in the first embodiment are used for them. A disposable diaper 36 of the present embodiment is provided with hook portions 24, which is the same as that in the first embodiment, at a hip portion 12. Slits 32, which are disposed in parallel with side portions 28, are defined at the side portions 28 of a belly portion 14. The slits 32 are disposed at portions opposed to the vicinity of base end portions of the connecting members 22.

The method for using the disposable diaper 36 of the present embodiment is the same as that of the first embodiment and has the same effects as that in the first embodiment. Since surface fasteners or the like are not provided to circumferences of the slits 32 of the belly portion 14, it can be manufactured by simple process and at a low cost. Further, it gives soft touch to the wearer when he puts it on.

Figure 5:
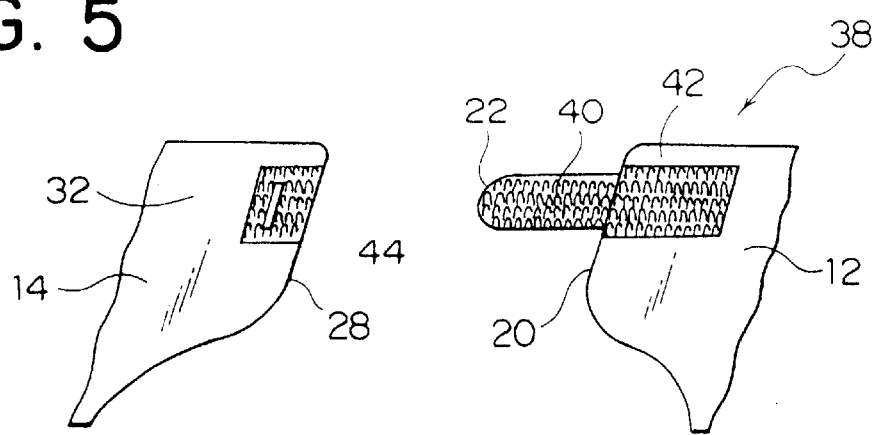
FIG. 5 is a partial perspective view of a disposable diaper according to a third embodiment of the present invention.

A third embodiment of the present invention will be explained below with reference to FIG. 5. With respect to the same members as those in the second embodiment, explanation is omitted and the same reference numbers as those in the first embodiment are used. In a disposable diaper 38 according to the present embodiment, side portions 20 of a hip portion 12 are provided with connecting members 22, which are elongated sideways, respectively. Surface fasteners 40 are disposed on outer surfaces of the connecting members 22. Surface fasteners 42 are disposed on an outer surface of the hip portion 12 near the base end portions of the connecting members 22. Both side portions 28 of a belly portion 14 are provided with surface fasteners 44 on an outer surface of the belly portion 14 at portions opposed to the base end portions of the connecting members 22. The surface fasteners 44 are provided with the slits 32 which are disposed in parallel with the side portions 28 and penetrate a diaper body 18.

In each of surface fasteners 40, 42 and 44, the hook portions and the loop portions are arranged in each line and they are engageable each other. For example, the surface fasteners 42 and 44 may be formed with the same arrangement of rows of hook portions and loop portions. while the surface fasteners 40 are formed with rows of loops and hooks to be opposed to and engaged with those of the surface fasteners 42 and 44 when the disposable diaper 38 is put on.

According to the present invention, a holding means can be composed of the surface fasteners 40, 42 and 44, which as the same shapes. Therefore, it is easy to manufacture the disposable diaper of the present embodiment.

Figure 6:
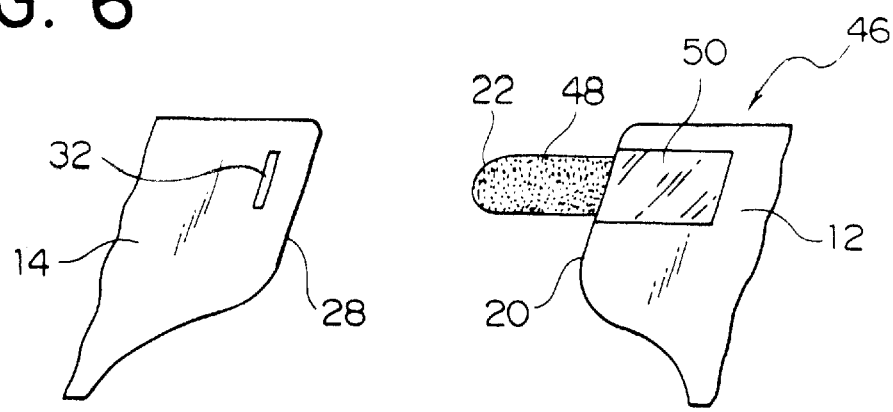
FIG. 6 is a partial perspective view of a disposable diaper according to a fourth embodiment of the present invention.

A fourth embodiment of the present invention will be explained below with reference to FIG. 6. With respect to the same members as those in the first embodiment, explanation is omitted and the same reference numbers as those in the third embodiment are used. In a disposable diaper 46 according to the present embodiment, side portions 20 of a hip portion 12 are provided with connecting members 22, which are elongated sideways respectively. Adhesives 48 are adhered on outer surfaces of the connecting members 22. Films 50, which are freely attachable to/detachable from the adhesives 48 and have flat and smooth surfaces, are disposed near the base end portions of the connecting members 22. Slits 32, which are disposed in parallel with side portions 28, are defined at portions opposed to the vicinity of the base end portions of the connecting members 22.

According to the disposable diaper 46 of the present embodiment, it is possible to manufacture it at a low cost, since it uses adhesives 48 as holding means.

The disposable diaper according to the present invention may not be limited to the embodiments as set forth above. Further, the connecting members 22 and the slits 32 may be disposed at either one of the hip portion 12 and the belly portion 14. For example, they may be disposed in reversed positions of the embodiments as set forth above. The connecting members 22 and the slits 32 may be disposed on both of the hip portion 12 and the belly portion 14, respectively. Further, the shapes of the connecting members 22, the holding means or the like can be freely changed. Moreover, a wearer of the disposable diaper according to the present invention may be a baby or an adult, in addition to an infant. The disposable diaper according to the present invention may be put on while wearer lies down as well as while the wearer is standing.

What is claimed:

1. A disposable diaper comprising:

a diaper body including a hip portion and a belly portion, which are spread out with a crotch portion between them;

a slit defined in a side portion of one of said hip portion and said belly portion;

a connecting member provided on a side portion of the other one of said belly portion and said hip portion to be elongated outwardly; and a holding means for connecting said hip portion and said belly portion by means of said connecting members when said connecting members are inserted into said slits and folded back.

2. A disposable diaper according to claim 1, wherein said holding means includes surface fasteners which are disposed on a face to be an inner surface when said connecting member is folded back and on a proximal portion of said connecting member, and the surface fasteners are adapted to be engaged with each other.

3. A disposable diaper according to claim 1, wherein said one of the holding means is also disposed on circumference of said slit.

* * * * *